United States Patent
Nowack (10) Patent No.: US 10,352,931 B2
(45) Date of Patent: Jul. 16, 2019

(54) DIAGNOSTIC DEVICE FOR THE DETECTION OF DISEASE RELATED TARGET STRUCTURES

(71) Applicant: GILUPI GmbH, Potsdam (DE)

(72) Inventor: Björn Nowack, Greifswald (DE)

(73) Assignee: GILUPI GMBH, Potsdam (DE)

( * ) Notice: Subject to any disclaimer, the term of this patent is extended or adjusted under 35 U.S.C. 154(b) by 562 days.

(21) Appl. No.: 14/914,875

(22) PCT Filed: Aug. 27, 2014

(86) PCT No.: PCT/EP2014/068135
§ 371 (c)(1),
(2) Date: Feb. 26, 2016

(87) PCT Pub. No.: WO2015/028489
PCT Pub. Date: Mar. 5, 2015

(65) Prior Publication Data
US 2016/0216257 A1 Jul. 28, 2016

(30) Foreign Application Priority Data
Aug. 27, 2013 (EP) .................................... 13181879

(51) Int. Cl.
*G01N 33/574* (2006.01)
*G01N 33/543* (2006.01)
*A61B 10/00* (2006.01)
*A61K 49/00* (2006.01)
*G01N 33/532* (2006.01)
*G01N 33/58* (2006.01)

(52) U.S. Cl.
CPC ... *G01N 33/54353* (2013.01); *A61B 10/0045* (2013.01); *A61K 49/0017* (2013.01); *A61K 49/0093* (2013.01); *G01N 33/532* (2013.01); *G01N 33/54306* (2013.01); *G01N 33/585* (2013.01); *G01N 33/574* (2013.01)

(58) Field of Classification Search
None
See application file for complete search history.

(56) References Cited

U.S. PATENT DOCUMENTS

| | | |
|---|---|---|
| 7,696,185 B2 | 4/2010 | Berkman |
| 8,846,580 B2 | 9/2014 | Pison et al. |
| 2004/0110723 A1 * | 6/2004 | Frangioni ............... C07F 5/025 514/64 |
| 2007/0041934 A1 | 2/2007 | William et al. |
| 2012/0237944 A1 | 9/2012 | Lucke et al. |
| 2013/0197334 A1 | 8/2013 | Weber et al. |
| 2014/0010758 A1 | 1/2014 | Berkmam et al. |
| 2014/0241985 A1 | 8/2014 | Berkman et al. |

FOREIGN PATENT DOCUMENTS

| | | |
|---|---|---|
| EP | 1811302 A1 | 7/2007 |
| WO | 2006131400 A1 | 12/2006 |
| WO | 2007106869 A1 | 9/2007 |
| WO | 2010145824 A1 | 12/2010 |
| WO | 2011113584 A1 | 9/2011 |
| WO | 2012064914 A2 | 5/2012 |
| WO | 2012174136 A1 | 12/2012 |

OTHER PUBLICATIONS

Lee et al (Prog. Polym. Sci 37:106-26 manuscript) (Year: 2012).*
Kasten et al., "Targeting prostate cancer cells with PSMA inhibitor-guided gold nanoparticles", Bioorganic & Medicinal Chemistry Letters, 2013, vol. 23, pp. 565-568.
Jackson et al., "Design and Pharmacological Activity of Phosphinic Acid Based NAALADase Inhibitors", Journal of Medicinal Chemistry, 2001, vol. 44, pp. 4170-4175.
Vitharana et al., "Synthesis and biological evaluation of (R)- and (S)-2-(phosphonomethyl)pentanedioic acids as inhibitors of glutamate carboxypeptidase II", Tetrahedron: Asymmetry, 2002, vol. 13, pp. 1609-1614.

* cited by examiner

*Primary Examiner* — Christopher M Gross
(74) *Attorney, Agent, or Firm* — The Webb Law Firm (57) ABSTRACT

The present invention provides a diagnostic device allowing highly specific and efficient in vivo and/or in vitro detection of a bio marker in a broad range of bodily fluids or tissues. The diagnostic device is composed of a binding agent that specifically binds a bio marker present in the bodily fluid linked by a linker compound or layer to the substrate, which includes a metallic, a semiconductor, or a polymeric carrier. The present invention further provides methods using said device for the detection of bio markers, as well as kits comprising said device and suitable ingredients for the detections of bio markers in a bodily fluid. Furthermore, the invention provides suitable in vivo and in vitro applications of said binding agent for the detection of specific disease-related target structures.

16 Claims, 4 Drawing Sheets
Specification includes a Sequence Listing.

SEQUENCE LISTING

<160> NUMBER OF SEQ ID NOS: 2

<210> SEQ ID NO 1
<211> LENGTH: 1321
<212> TYPE: PRT
<213> ORGANISM: Tetraodon nigroviridis

<400> SEQUENCE: 1

Met Ile Lys Ile Leu Ile Ser Leu Leu Cys Cys Ala Val Leu Phe Thr
1               5                   10                  15

Val Gly Ile Leu Ile Gly His Tyr Ala Ile Pro Arg Ser Ser Thr Pro
                20                  25                  30

Pro Pro Ser Trp Leu Thr Glu Val Ala Lys Asp Val Asp Glu Ser Phe
            35                  40                  45

Ile Glu Ala Phe Leu Ser Glu Val Asn Asn Leu Gln Ile Gln Glu Asn
    50                  55                  60

Leu Lys Glu Leu Thr Lys Ala Pro His Met Ala Thr Thr Pro Gly Asp
65                  70                  75                  80

Glu Asp Thr Val Asn Tyr Met Leu Lys Arg Trp Gln Asp Pro Asp Ser
                85                  90                  95

Gly Leu Asp Gln Ala Trp Arg Glu Glu Tyr Met Val Tyr Leu Ser Phe
            100                 105                 110

Pro Asp Pro Gln Asn Pro Asn Lys Val Thr Val Val Asn Ser Ser Gly
        115                 120                 125

Glu Val Leu His Thr Val Arg Glu Lys Glu Lys Asn Tyr Thr Ser Asp
    130                 135                 140

Gln Asn Asp Pro Glu Val Val Gln Pro Tyr Ala Ala Tyr Ser Pro Pro
145                 150                 155                 160

Gly Thr Pro Lys Gly Lys Leu Val Tyr Ala Asn Gln Gly Lys Pro Ser
                165                 170                 175

Asp Tyr Gln Gln Leu Val Asn Gln Gly Val Asp Leu Arg Asn Thr Ile
            180                 185                 190

Ala Ile Thr Arg Tyr Gly Gly Ala Gly Arg Ala Ala Lys Ala Ile Asn
        195                 200                 205

Ala Ala Pro Tyr Gly Val Val Gly Val Leu Val Tyr Thr Asp Pro Leu
    210                 215                 220

```
Asp Ile Asn Asp Asp Leu Met Ser Asp Phe Asn Glu Thr Tyr Pro His
225                 230                 235                 240

Ser Trp Tyr Met Pro Pro Ser Gly Val Glu Arg Gly Ser Phe Ala Thr
            245                 250                 255

Asn Tyr Gly Asp Pro Leu Thr Pro Tyr Leu Ala Ala Lys Glu Gly Thr
        260                 265                 270

Tyr Arg Ile Ser Pro Glu Asn Ile Thr Gly Ile Pro Pro Ile Pro Ile
    275                 280                 285

Gln Pro Ile Gly Phe Glu Asp Ala Tyr Met Leu Ile Trp Phe Val Met
290                 295                 300

Ala Gln Leu Asp Gly Asp Lys Ala Pro Val Asp Trp Gln Gly Ser Phe
305                 310                 315                 320

Asn Cys Ser Tyr Asn Phe Gly Gly Pro Gly Phe Lys Asn Thr Ser Ala
                325                 330                 335

Phe Ser Gly Ser Asp Val Gln Leu Asn Ile Ser Asn Tyr Gly Glu Ile
            340                 345                 350

Arg Asn Ser Ser Asn Val Met Gly Val Ile Arg Gly Ser Val Glu Pro
        355                 360                 365

Asp Arg Tyr Val Ile Tyr Gly Asn His Arg Asp Ser Trp Val His Gly
    370                 375                 380

Ala Ile Asp Pro Ser Ser Gly Thr Ser Val Met Leu Glu Leu Ser Arg
385                 390                 395                 400

Val Leu Gly Ala Lys Val Lys Gln Gly Lys Trp Arg Pro Arg Arg Ser
                405                 410                 415

Ile Ile Phe Gly Ser Trp Gly Ala Glu Glu Phe Gly Leu Ile Gly Ser
            420                 425                 430

Ala Glu Tyr Thr Glu Gln Tyr Leu Pro Lys Leu Ser Gln Arg Thr Val
        435                 440                 445

Ala Tyr Ile Asn Val Asp Ile Ala Val Phe Ala Asn Ala Thr Leu Arg
    450                 455                 460

Ala Ser Gly Met Pro Ser Val Gln Asn Val Ile Phe Lys Ala Ala Lys
465                 470                 475                 480

Gln Val Asn Ala Pro Gly Val Asp Ser Thr Ser Val Tyr Glu Asn Trp
                485                 490                 495

Met Lys Tyr Ser Asn Arg Thr Ser Pro Glu His Gly Thr Ile Pro Arg
            500                 505                 510

Met Gly Tyr Trp Ile Gly Gln Glu Val Ile Thr Leu Pro Ser Ser Ile
        515                 520                 525

Thr Trp Glu Ser Gln Pro Trp Thr Cys Pro Thr Arg Met Thr Gly Val
    530                 535                 540

Lys Gln Arg Ser His Leu Arg Cys Leu Pro His Gly Leu Arg His Arg
545                 550                 555                 560

Arg Leu Leu Leu Gln Val Ile Asp Pro Gly Phe Val Ser His Gln Ala
                565                 570                 575

Val Ala Arg Thr Ala Gly Asn Ala Leu Ile Arg Leu Ala Asp Ser Leu
            580                 585                 590

Val Leu Pro Leu Asn Cys Ser Asp Tyr Ala Glu Gly Leu Glu Asp Tyr
        595                 600                 605

Leu Arg Thr Ala Val Gly Leu Tyr Glu Gly Gln Leu Gln Met Trp Asn
    610                 615                 620

Ile Ser Met Gly Asn Pro Val Thr His Ala Leu Ile Arg Asn Asn Ala
625                 630                 635                 640
```

-continued

Glu Arg Glu Tyr Ser Lys Thr Lys Thr Thr Phe Cys Phe Val Phe Thr
                    645                 650                 655

Glu Pro Leu Lys Ser Ala Val Ala Asn Phe Arg Lys Ala Ala Thr Arg
            660                 665                 670

Met Asp Arg Thr Ile His Ser Leu Asp Leu Ala Asn Glu Thr Pro Leu
        675                 680                 685

Lys Val Arg Lys Ile Asn Asp Gln Leu Met Leu Leu Asp Arg Ala Phe
    690                 695                 700

Leu Asp Pro Leu Ala Phe Pro Asp Lys Tyr Ala Phe Arg His Val Ile
705                 710                 715                 720

Trp Ala Ser Ser Ala Gly Lys Leu Thr Phe Pro Gly Leu Ala Asp
                725                 730                 735

Ala Phe Ala Ser Ala Asn Asn Ser Leu Gly Glu Pro Ser Ala Gln His
            740                 745                 750

Lys Val His Tyr His Leu Ser Val Leu Ser Gln Ala Ile Asp Ser Ala
        755                 760                 765

Ala Asn Thr Leu Asp Glu Ala Pro Gly Arg Cys Ala Asp Ala Ile Asn
    770                 775                 780

Ala Ala Pro Tyr Gly Val Val Gly Val Leu Val Tyr Thr Asp Pro Leu
785                 790                 795                 800

Asp Ile Asn Asp Ser Leu Met Ser Asp Phe Asn Glu Thr Tyr Pro His
                805                 810                 815

Ser Trp Tyr Met Pro Pro Ser Gly Val Glu Arg Gly Ser Phe Ala Thr
            820                 825                 830

Asn Tyr Gly Asp Pro Leu Thr Pro Tyr Leu Ala Ala Lys Glu Gly Thr
        835                 840                 845

Tyr Arg Ile Ser Pro Glu Asn Ile Thr Gly Ile Pro Pro Ile Pro Ile
    850                 855                 860

Gln Pro Ile Gly Phe Glu Asp Ala Tyr Met Leu Ile Trp Phe Val Met
865                 870                 875                 880

Ala Gln Leu Asp Gly Asp Lys Ala Pro Val Asp Trp Gln Gly Ser Phe
                885                 890                 895

Asn Cys Ser Tyr Asn Phe Gly Gly Pro Gly Phe Lys Asn Thr Ser Ala
            900                 905                 910

Phe Ser Gly Ser Asp Val Gln Leu Asn Ile Ser Asn Tyr Gly Glu Ile
        915                 920                 925

Arg Asn Ser Ser Asn Val Met Gly Val Ile Arg Gly Ser Val Glu Pro
    930                 935                 940

Asp Arg Tyr Val Ile Tyr Gly Asn His Arg Asp Ser Trp Val His Gly
945                 950                 955                 960

Ala Ile Asp Pro Ser Ser Gly Thr Ser Val Met Leu Glu Leu Ser Arg
                965                 970                 975

Val Leu Gly Ala Lys Gln Tyr Leu Pro Lys Leu Ser Gln Arg Thr Val
            980                 985                 990

Ala Tyr Ile Asn Val Asp Ile Ala  Val Phe Ala Asn Ala  Thr Leu Arg
        995                 1000                 1005

Ala Ser  Gly Met Pro Ser Val  Gln Asn Val Ile Phe  Lys Ala Ala
    1010                 1015                 1020

Lys Gln Val Asn Ala Pro Gly  Val Asp Ser Thr Ser  Val Tyr Glu
    1025                 1030                 1035

Asn Trp  Met Lys Tyr Ser Asn  Arg Thr Ser Pro Glu  His Gly Thr
        1040                 1045                 1050

```
Ile Pro Arg Met Gly Tyr Leu Asn Gly Ala Gly Ser Asp Tyr Ala
1055                1060                1065
Ala Phe Val His Tyr Leu Gly Ile Thr Ala Met Asp Leu Ser Tyr
1070                1075                1080
Thr Tyr Asp Arg Ser Lys Thr Asn Ala Arg Ile Tyr Pro Ala Tyr
1085                1090                1095
His Thr Ala Tyr Asp Thr Phe Asp Tyr Cys Ser Lys Tyr Ile Asp
1100                1105                1110
Pro Gly Phe Val Ser His Gln Ala Val Ala Arg Thr Ala Gly Asn
1115                1120                1125
Ala Leu Ile Arg Leu Ala Asp Ser Leu Val Leu Pro Leu Asn Cys
1130                1135                1140
Ser Asp Tyr Ala Glu Gly Leu Glu Asp Tyr Leu Arg Thr Ala Val
1145                1150                1155
Gly Leu Tyr Glu Gly Gln Leu Gln Met Trp Asn Ile Ser Met Gly
1160                1165                1170
Asn Pro Val Thr His Ala Leu Ile Arg Asn Asn Ala Glu Arg Glu
1175                1180                1185
Tyr Ser Lys Thr Lys Thr Thr Phe Cys Phe Val Phe Thr Glu Pro
1190                1195                1200
Leu Lys Ser Ala Val Ala Asn Phe Arg Lys Ala Ala Thr Arg Met
1205                1210                1215
Asp Arg Thr Ile His Ser Leu Asp Leu Ala Asn Glu Thr Pro Leu
1220                1225                1230
Lys Val Arg Lys Ile Asn Asp Gln Leu Met Leu Leu Asp Arg Ala
1235                1240                1245
Phe Leu Asp Pro Leu Ala Phe Pro Asp Lys Tyr Ala Phe Arg His
1250                1255                1260
Val Ile Trp Ala Ser Ser Ser Ala Gly Lys Ser Thr Phe Pro Gly
1265                1270                1275
Leu Ala Asp Ala Phe Ala Ser Ala Asn Asn Ser Leu Gly Glu Pro
1280                1285                1290
Ser Ala Gln His Lys Val His Tyr His Leu Ser Val Leu Ser Gln
1295                1300                1305
Ala Ile Asp Ser Ala Ala Asn Thr Leu Asp Glu Val Ile
1310                1315                1320

<210> SEQ ID NO 2
<211> LENGTH: 3966
<212> TYPE: DNA
<213> ORGANISM: Tetraodon nigroviridis

<400> SEQUENCE: 2
atgataaaga ttttgatctc gctgctgtgc tgcgctgttc tttttacagt gggcatcttg      60
attggccact atgccatccc cagaagcagc accccgccgc cgtcctggct gacagaggtg     120
gccaaggatg tggacgagag cttcatcgag gcctttttat ctgaggtgaa caacctgcaa     180
atccaggaaa acctgaagga gctgacaaaa gcgccccaca tggccacgac acccggagac     240
gaagacacgg taaattacat gctgaagagg tggcaggatc ctgattcggg tctggaccag     300
gcctggaggg aggaatacat ggtctacttg tccttccccg atccccaaaa ccccaacaag     360
gtcacagtgg tgaactcgtc tggggaggtc ttgcacactg tcagagagaa agagaagaac     420
tacacctcag accaaaatga cccagaggtg gttcagccct acgctgcata ctcgcccccc     480
ggaacgccaa agggtaaact agtgtacgcc aaccagggga aacccagtga ctaccagcag     540
```

```
ctggtcaacc agggagtgga cctgagaaac accatcgcca tcaccagata cggaggagca    600
gggcgagctg ctaaagcgat caatgcggcc ccctacggtg tcgtgggcgt gctcgtctac    660
accgaccctt tagacatcaa cgacgatctg atgtcggact tcaatgagac gtatcctcac    720
tcctggtaca tgccgccatc tggtgtggag agaggcagtt tcgccaccaa ctacggagac    780
ccgctgaccc cctacctggc tgccaaagag ggaacgtaca gaatttcacc tgagaacatc    840
acgggtatcc ctcccattcc gatccagcca atcggattcg aggacgccta catgctcatt    900
tggtttgtga tggcccagct ggatggagac aaggctccgg tcgactggca gggttcattt    960
aactgctcct acaactttgg cggccctgga tttaaaaaca catctgcgtt cagtggaagt   1020
gacgtgcagc taaacatctc caactacggg gaaataagga actcctctaa cgtgatgggt   1080
gttatcagag ggagtgtcga gccagacagg tacgtgatct acggcaacca cagggacagc   1140
tgggtgcacg cgccatcga ccccagcagc gggacatcgg tgatgctgga gctgagcaga   1200
gtgttgggtg ccaaggtcaa gcagggaaaa tggaggccgc gccggtcaat catcttcgga   1260
agctgggggg ctgaggagtt tggtctgatc ggttctgcag aatacacaga gcaatattta   1320
cccaaaactca gccaacggac ggttgcctac atcaacgtgg acatagctgt ctttgccaac   1380
gccaccctca gagcctcggg gatgccgtcg gtgcagaacg tcatcttcaa agccgcaaaa   1440
caggttaacg cccccggagt ggattcaacg tctgtgtatg aaaactggat gaaatattcc   1500
aacaggacca gccggagca cgggaccatt cccaggatgg gatactggat tgggcaggaa   1560
gtgattacgc tgccttcgtc cattacctgg gaatcacagc catggacctg tcctacacgt   1620
atgcacaggag taaacaacg ctcgcatcta cgctgcctac cacacggcct acgacaccgt   1680
cgactactgc tccaagtaat cgatcctggg ttcgtcagtc accaggccgt ggccaggacg   1740
gcagggaacg ccctgatccg gctggccgac agcctggtgc tgccgctgaa ctgcagcgac   1800
tacgccgagg gtctggagga ctacctgagg accgcgtgg gcctgtatga gggtcagctg   1860
cagatgtgga acatctccat gggtaaccct gtcacgcacg ccctgattag aaacaatgct   1920
gaaagagaat attcaaaaac aaaaacaacc ttctgctttg tctttacaga acctcttaaa   1980
agtgcggtgg ccaactttcg taaggccgcc actcgtatgg accggacgat ccacagtttg   2040
gacctggcaa atgagacccc actgaaggtc agaaagatca cgaccagct gatgctgctg   2100
gaccgagctt tcttggaccc tctggccttt cctgacaaat atgcattcag gcacgttatc   2160
tgggcttcca gtagtgccgg taagctgacc tttccgggtt tggccgatgc cttcgccagt   2220
gctaacaact cactgggaga gcccagcgcc agcacaagg tgcactacca cctgtcagtg   2280
ctgagccagg ccatcgacag cgccgccaac accctggatg aggcaccagg aagatgcgct   2340
gacgcgatca atgcggcccc ctacggtgtc gtgggcgtgc tcgtctacac cgaccccttta   2400
gacatcaacg acagtctgat gtcggacttc aatgagacgt atcctcactc ctggtacatg   2460
ccgccatctg gtgtggagag aggcagtttc gccaccaact acggagaccc gctgacccc   2520
tacctggctg ccaaagaggg aacgtacaga atttcacctg agaacatcac gggtatccct   2580
cccattccga tccagccaat cggattcgag gacgcctaca tgctcatttg gtttgtgatg   2640
gcccagctgg atggagacaa ggctccggtc gactggcagg gttcatttaa ctgctcctac   2700
aactttggcg gccctggatt taaaaacaca tctgcgttca gtggaagtga cgtgcagcta   2760
aacatctcca actacgggga aataaggaac tcctctaacg tgatgggtgt tatcagaggg   2820
agtgtcgagc cagacaggta cgtgatctac ggcaaccaca gggacagctg gtgcacggc   2880
gccatcgacc ccagcagcgg gacatcggtg atgctggagc tgagcagagt gttgggtgcc   2940
```

```
aagcaatatt tacccaaact cagccaacgg acggttgcct acatcaacgt ggacatagct    3000
gtctttgcca acgccaccct cagagcctcg gggatgccgt cggtgcagaa cgtcatcttc    3060
aaagccgcaa aacaggttaa cgcccccgga gtggattcaa cgtctgtgta tgaaaactgg    3120
atgaaatatt ccaacaggac cagcccgag cacgggacca ttcccaggat gggatacctg     3180
aatggagcag gaagtgatta cgctgccttc gtccattacc tgggaatcac agccatggac    3240
ctgtcctaca cgtatgacag gagtaaaacc aacgctcgca tctaccctgc ctaccacacg    3300
gcctacgaca ccttcgacta ctgctccaag tacatcgatc ctgggttcgt cagtcaccag    3360
gccgtggcca ggacggcagg gaacgccctg atccggctgg ccgacagcct ggtgctgccg    3420
ctgaactgca gcgactacgc cgagggtctg gaggactacc tgaggaccgc cgtgggcctg    3480
tatgagggtc agctgcagat gtggaacatc tccatgggta accctgtcac gcacgccctg    3540
attagaaaca atgctgaaag agaatattca aaaacaaaaa caaccttctg ctttgtcttt    3600
acagaacctc ttaaaagtgc ggtggccaac tttcgtaagg ccgccactcg tatggaccgg    3660
acgatccaca gtttggacct ggcaaatgag accccactga aggtcagaaa gatcaacgac    3720
cagctgatgc tgctggaccg agctttcttg gaccctctgg cctttcctga caaatatgca    3780
ttcaggcacg ttatctgggc ttccagtagt gccggtaagt cgacctttcc gggtttggcc    3840
gatgccttcg ccagtgctaa caactcactg ggagagccca gcgcccagca caaggtgcac    3900
taccacctgt cagtgctgag ccaggccatc gacagcgccg ccaacaccct ggatgaggtc    3960
atatag                                                               3966
```

DIAGNOSTIC DEVICE FOR THE DETECTION OF DISEASE RELATED TARGET STRUCTURES

CROSS-REFERENCE TO RELATED APPLICATIONS

This application is the United States national phase of PCT International Application No. PCT/EP2014/068135 filed Aug. 27, 2014, and claims priority to European Patent Application No. 13181879.1, filed Aug. 27, 2013, the disclosure of each of which is hereby incorporated by reference in its entirety.

The Sequence Listing associated with this application is filed in electronic format via EFS-Web and is hereby incorporated by reference into the specification in its entirety. The name of the text file containing the Sequence Listing is 1600934_ST25.txt. The size of the text file is 17,077 bytes, and the text file was created on Feb. 23, 2016.

BACKGROUND OF THE INVENTION

Field of the Invention

The present invention relates to a diagnostic device for the in vivo and/or in vitro detection of a bio marker in a fluid or tissue comprising a binding agent that specifically binds said bio marker, a linker compound, and a substrate composed of a metallic, a semiconductor, or a polymeric carrier, wherein the binding agent is an enzyme inhibitor. The present invention further relates to a method for detecting bio markers in a fluid or tissue using the diagnostic device of the invention, as well as kits for detecting disease related bio markers comprising the diagnostic device of the invention. The invention further relates to the use of said binding agents for the detection of specific disease-related target structures.

Many bio markers, such as specific cell types, small molecules, bacteria, and viruses are present in human bodily fluids. However, due to their low concentrations, they are not detectable in an efficient way by the use of known enrichment methods, so they cannot be used for conventional diagnostic methods, such as detection methods established in clinical chemistry, pathology, and cytology.

Bio markers, for example circulating tumor cells present in a blood sample are detected in vitro by commercially available methods using immunocytochemical approaches. Antibodies specific to epithelial antigens such as CK or EpCAM are generally the most widely used markers for epithelial tumor cell detection despite variable rates of false-positive and -negative staining. For instance, the percentage of CK-positive cells in normal controls range from 0 to 20% in instances of non-specific binding of non-tumoural cells or in instances of specific binding to circulating epithelial cells, which are present due to trauma or inflammation within the body. Due to non-specific binding, specificity is limited, and the sample volume necessary for the detection of the bio marker is very high. Furthermore, antibody-based techniques involve high costs for preparing the antibody necessary for detection.

A further drawback of antibody-based techniques is that the antibody can only be removed from the antigen under strong conditions (with respect to high salt conditions, heat, pH-value) which is highly detrimental for the cell. In contrast, the binding agent of the invention may be easily resolved in high concentrations under normal conditions, thereby releasing the binding agent bound to the linker. Therefore, these techniques are less suitable for in vitro detection of biomarkers.

Therefore, there is a need in alternative diagnostic devices which do not have the drawbacks of the detection devices and methods known in the art.

SUMMARY OF THE INVENTION

The object of the invention is to provide detection devices that not only detect rare bio markers in bodily fluids, but also to provide an efficient way of binding and/or enrichment of bio markers on a substrate suitable for diagnosis of various target structures specific for diseases, such as infection or cancer.

Compared to the antibody-based detection methods, the costs for the diagnostic device of the invention comprising the binding-agent prepared by organic synthesis are supposed to be lower. In particular, the binding agent of the invention can be prepared more efficiently in an industrial scale. Furthermore, specificity of the system of the invention is improved due to the single binding site provided by the linker. Small molecules such as the inhibitor cannot be detected by the immune system and therefore have a lower risk for side effects when administered into the body.

The solution to the above technical problem is achieved by the embodiments characterized below and in the appended claims.

In a first embodiment the invention relates to a diagnostic device for the in vivo and/or in vitro detection of a bio marker in a fluid or tissue comprising a composition having the formula:

$$A\text{-}L\text{-}B,$$

wherein A is a binding agent that specifically binds said bio marker; L is a linker; and B is a substrate comprising a metallic, a semiconductor, or a polymeric carrier. In a preferred embodiment A is an enzyme inhibitor as defined herein below.

In another embodiment, the herein described bio marker may have a target structure which is present on a protein, quorum sensing molecule, toxin, lipid, carbohydrate, nucleic acid, small molecule, drug, bacteria, virus or eukaryotic cell.

In another embodiment, the invention relates to the diagnostic device as described herein, wherein the herein described bio marker has a target structure which is present on a circulating tumor cell (CTC) in the bodily fluid.

In another embodiment, the target structure is glutamate carboxypeptidase II.

The invention is further directed to a diagnostic device as described herein, wherein the binding agent A has a target structure related to a disease. Preferably, the disease is cancer or infection.

In a further embodiment of the diagnostic device of the invention, A is an inhibitor of the enzyme activity of glutamate carboxypeptidase II. Preferably the inhibition of the enzyme activity of glutamate carboxypeptidase II is reversible.

In another embodiment, the invention relates to the diagnostic device as described herein, wherein A has the following structural formula II:

wherein X is a bond, NH or O, $R_1$, $R_2$, $R_3$, $R_4$ and $R_5$ are independently selected from the group consisting of: hydrogen, alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, 4° ammonium ion, primary ketamine, secondary ketamine, primary aldimine, secondary aldimine, imide, azide, azo (diimide), cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphine, phosphono, phosphate, borono, boronate, borino, and borinate.

In another embodiment, the invention relates to the diagnostic device as described herein, wherein $R_1$ or $R_2$ as defined herein is a group bonded covalently or non-covalently to L.

A preferred embodiment of the invention relates to the herein described diagnostic device, wherein A has the following structural formula III:

In a further embodiment, the linker compound L of the diagnostic device of the invention is a polymer, protein, preferably alginate or hydrogel.

According to a further embodiment of the invention, the binding agent A is conjugated to a detectable marker, preferably a fluorescent dye or a chemiluminescent dye or a radiotracer; or the binding agent A is conjugated to a drug. Preferably, the drug is an anti cancer drug.

In another embodiment, the diagnostic device of the invention comprises a substrate (herein indicated as B), wherein the substrate comprises a metallic carrier. Preferably, the metallic carrier is composed of stainless steel.

In a further embodiment, the diagnostic device of the invention comprises an interlayer assembled on the substrate B. Preferably the interlayer is composed of a noble metal like gold, platinum or silver.

In a further embodiment, the invention relates to a method for detecting bio markers in a fluid or tissue comprising the steps: a) contacting the binding agent of Formula II or III or the diagnostic device of the invention with a bodily fluid sample or tissue; b) allowing the A to bind to the bio marker in the bodily fluid or tissue; and c) detecting the presence of A.

In a further embodiment, the invention relates to a kit for detecting disease related bio markers in a fluid or tissue comprising: a) the diagnostic device of the invention, and b) instructions for its use.

In a further embodiment, the invention relates to the use of the binding agent of formula II or III or the diagnostic device of the invention for the detection of specific disease related target structures.

DETAILED DESCRIPTION OF THE INVENTION

In a first embodiment, the invention relates to a diagnostic device for the in vivo and/or in vitro detection of a bio marker in a fluid or tissue comprising a composition having the formula I:

A-L-B, wherein A is a binding agent that specifically binds said bio marker, wherein the binding agent is an enzyme inhibitor; L is a linker; and B is a substrate comprising a metallic, a semiconductor, or a polymeric carrier.

The term "diagnostic device" as used herein, refers to a device used for diagnosis or detection of bio markers; e.g. in clinical chemistry, pathology, and cytology. For example, the diagnostic device of the invention may be used for primary risk assessment (predictive and early disease identification), prognosis, therapeutic selection, disease or condition monitoring and management, population genetics screening and monitoring, pharmacogenomic diagnostics, epidemiological studies and monitoring, clinical trials monitoring, and syndromic surveillance including clinical analyzers, portable battery operated meters, self-performing assay devices, point of care analyzers, point of care meters, point of present analyzers, point of present meters, etc. . .

The term "bio marker" as used herein, refers to a substance having a target structure, preferably a biological molecule or substance present in a bodily fluid of a patient. Examples for bio markers are peptides, proteins, quorum sensing molecules, toxins, lipids, carbohydrates, nucleic acids, small molecules, drugs, bacteria, viruses, eukaryotic cells.

The term "target structure" as used herein refers to a microscopic or submicroscopic structure, for example, in a bodily fluid of a patient, to which it is desired to bind a binding agent attached to the diagnostic device of the invention. The term "target structure" as used herein may designate an entire cell, but more particularly denotes a cellular structure, i.e., an organic molecule such as a protein, nucleotide chain, carbohydrate, or lipid, which is located inside a biological cell, on a cell membrane, in intercellular spaces, or in a body fluid such as blood or lymph. The term "cellular structure" concomitantly also denotes a larger structure such as a cell or virus.

In another embodiment, the invention relates to the diagnostic device as described herein, wherein the bio marker has a target structure which is present on a peptide, protein, quorum sensing molecule, toxin, lipid, carbohydrate, nucleic acid, small molecule, drug, bacteria, virus or eukaryotic cell; e.g. alcohol dehydrogenase (ADH), epithelial growth factor receptor (EGFR), prostate specific antigen (PSA), prostate specific membrane antigen (PSMA), *Escherichia coli, Staphylococcus aureus, Pseudomonas* spec., Papilloma virus, human immunedeficient virus (HIV), homoserin lactones, tetrahydrocannabinol (THC), circulating tumor cell (CTC).

In another embodiment, the invention relates to the diagnostic device as described herein, wherein the herein described bio marker has a target structure which is present on a circulating tumor cell (CTC) in the bodily fluid.

The terms "circulating tumor cell or CTC" as used herein, refer to any circulating cancer cell that is found in a sample obtained from a subject. Typically, CTCs have been shed from a solid tumor. As such, CTCs are often epithelial cells shed from solid tumors that are found in very low concentrations in the circulation of patients with advanced cancers. CTCs may also be mesothelial cells from sarcomas or melanocytes from melanomas.

The term "bodily fluid" as used herein, is intended to mean a naturally occurring fluid from an animal, or human such as saliva, sputum, serum, plasma, blood, urine, mucus, gastric juices, pancreatic juices, semen, products of lactation or menstruation, tears, or lymph.

As used herein, "a target structure," refers to any rationally selected sequence or combination of sequences in which the sequences or sequence(s) are chosen based on a three-dimensional configuration that is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

In another embodiment, the target structure is glutamate carboxypeptidase II or a fragment thereof. Preferably, the target structure is EC 3.4.17.21-Glutamate carboxypeptidase II or a fragment thereof. The nucleotide and amino acid sequences of EC 3.4.17.21-Glutamate carboxypeptidase II is shown as SEQ ID NOs: 1 and 2.

The invention is further directed to a diagnostic device as described herein, wherein the binding agent A has a target structure related to a disease. In a preferred embodiment, the disease is cancer or infection.

The term "cancer" as used herein refers to a metastatic and/or a non-metastatic cancer, especially solid tumor cancer, in a subject, and includes primary and secondary cancers. Reference to cancer includes reference to cancer cells. The term "solid tumor cancer" as used herein refers to a cancer resulting in one or more solid tumors composed of cancer cells and includes, for example, lung cancer, brain (glioblastomas, medulloblastoma, astrocytoma, oligodendroglioma, ependymomas), liver, thyroid, bone, adrenal, spleen, kidney, lymph node, small intestine, pancreas, colon, stomach, breast, endometrium, prostate, testicle, ovary, skin, head and neck, and esophagus.

The term "infection" as used herein refers to the invasion of a subject. The term encompasses excessive growth of microbes that are normally present in or on the body of the subject. More generally, a microbial infection can be any situation in which the presence of a microbial population(s) is damaging to a host organism (subject). Thus, an organism is "suffering" from a microbial infection when excessive numbers of a microbial population are present in or on the organism's body, or when the effects of the presence of a microbial population(s) is damaging the cells or other tissue of an organism.

A "subject", as used herein, is an individual indented for diagnosis, such as predictive and early disease identification. Subjects of interest herein include plants, animals or humans; preferably humans.

In another embodiment, the binding agent A of the invention is an inhibitor, preferably an enzyme inhibitor. An "inhibitor", as used herein refers to a compound that binds to an active site or elsewhere within or on the surface of the bio marker, thereby blocking its activity.

The term "enzyme inhibitor", used herein refers to a molecule reducing an enzyme activity through binding to an enzyme. The enzyme inhibitor binds to an active site or elsewhere within or on the surface of an enzyme, thereby blocking an interaction of the enzyme with a substrate and may be bound to the enzyme in a reversible or irreversible manner. Preferably, the inhibitor of the invention binds in a reversible manner.

The term "reversible" as used herein means capable of being returned to the original ("unbound") condition. The term "reversible inhibition" as used herein means that the inhibitory effect is such that the binding agent maintains the ability to inhibit the activity of the target molecule (bio marker).

Figure 1:
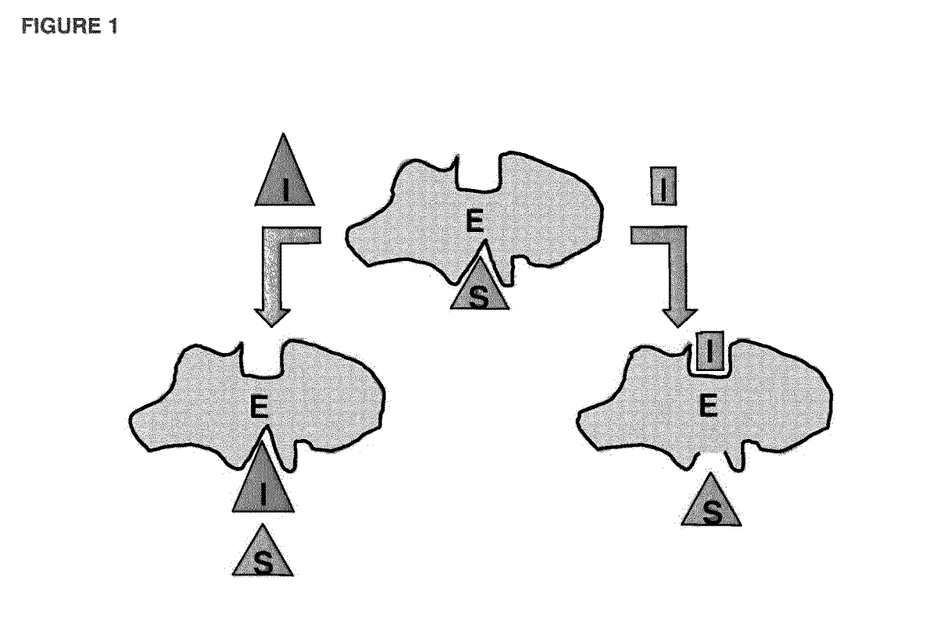
FIG. 1 shows a schematic illustration of an interaction between a possible inhibitor for an enzyme with a competitive inhibition.

FIG. 1 simplifies binding possibilities of a possible inhibitor for an enzyme with a competitive inhibitions (left) respectively allosteric inhibition (right) with E=Enzym, I=Inhibitor, S=natural substrate)

The binding agent A of the invention may be any kind of reversible or irreversible inhibitor of an enzyme activity as defined below. Preferably, the binding agent of the invention inhibits activity of an enzyme in a reversible manner.

Types of Reversible Inhibitors

Reversible inhibitors bind to enzymes with non-covalent interactions such as hydrogen bonds, hydrophobic interactions and ionic bonds. Multiple weak bonds between the inhibitor and the active site combine to produce strong and specific binding. In contrast to substrates and irreversible inhibitors, reversible inhibitors generally do not undergo chemical reactions when bound to the enzyme and can be easily removed by dilution or dialysis.

There are four kinds of reversible enzyme inhibitors. They are classified according to the effect of varying the concentration of the enzyme's substrate on the inhibitor.

a. In competitive inhibition, the substrate and inhibitor cannot bind to the enzyme at the same time, as shown in the figure on the left. This usually results from the inhibitor having an affinity for the active site of an enzyme where the substrate also binds; the substrate and inhibitor compete for access to the enzyme's active site. This type of inhibition can be overcome by sufficiently high concentrations of substrate (Vmax remains constant), i.e., by out-competing the inhibitor. However, the apparent Km will increase as it takes a higher concentration of the substrate to reach the Km point, or half the Vmax. Competitive inhibitors are often similar in structure to the real substrate (see examples below).

b. In uncompetitive inhibition, the inhibitor binds only to the substrate-enzyme complex, it should not be confused with non-competitive inhibitors. This type of inhibition causes Vmax to decrease (maximum velocity decreases as a result of removing activated complex) and Km to decrease (due to better binding efficiency as a result of Le Chatelier's principle and the effective elimination of the ES complex thus decreasing the Km which indicates a higher binding affinity).

c. In mixed inhibition, the inhibitor can bind to the enzyme at the same time as the enzyme's substrate. However, the binding of the inhibitor affects the binding of the substrate, and vice versa. This type of inhibition can be reduced, but not overcome by increasing concentrations of substrate. Although it is possible for mixed-type inhibitors to bind in the active site, this type of inhibition generally results from an allosteric effect where the inhibitor binds to a different site on an enzyme. Inhibitor binding to this allosteric site changes the conformation (i.e., tertiary structure or three-dimensional shape) of the enzyme so that the affinity of the substrate for the active site is reduced.

d. Non-competitive inhibition is a form of mixed inhibition where the binding of the inhibitor to the enzyme reduces its activity but does not affect the binding of substrate. As a result, the extent of inhibition depends only on the concentration of the inhibitor. Vmax will decrease due to the inability for the reaction to proceed as efficiently, but Km will remain the same; as the actual binding of the substrate, by definition, will still function properly.

Types of Irreversible Inhibition

Irreversible inhibitors usually covalently modify an enzyme, and inhibition can therefore not be reversed. Irreversible inhibitors often contain reactive functional groups such as nitrogen mustards, aldehydes, haloalkanes, alkenes, Michael acceptors, phenyl sulfonates, or fluorophosphonates. These electrophilic groups react with amino acid side chains to form covalent adducts. The residues modified are those with side chains containing nucleophiles such as hydroxyl or sulfhydryl groups; these include the amino acids serine, cysteine, threonine or tyrosine.

Irreversible inhibition is different from irreversible enzyme inactivation. Irreversible inhibitors are generally specific for one class of enzyme and do not inactivate all proteins; they do not function by destroying protein structure but by specifically altering the active site of their target. For example, extremes of pH or temperature usually cause denaturation of all protein structure, but this is a non-specific effect. Similarly, some non-specific chemical treatments destroy protein structure: for example, heating in concentrated hydrochloric acid will hydrolyse the peptide bonds holding proteins together, releasing free amino acids.

Irreversible inhibitors display time-dependent inhibition and their potency therefore cannot be characterised by an IC50 value. This is because the amount of active enzyme at a given concentration of irreversible inhibitor will be different depending on how long the inhibitor is pre-incubated with the enzyme.

Examples of inhibitors can be found in the Table 1 below:

TABLE 1

| Inhibitor | IC$_{50}$ |
|---|---|
| (R)-2-(phosphonomethyl)-pentanedioic acid | 0.000030 mM |
| (S)-2-(3-mercaptopropyl)-pentanedioic acid | 0.000067 mM |
| (S)-2-(hydroxypentafluorophenylmethyl-phosphinoylmethyl)pentanedioic acid | 0.000034 mM |
| (S)-2-(phosphonomethyl)-pentanedioic acid | 0.0000001 mM |
| 2-(3-mercaptopropyl)-pentanedioic acid | 90 nM |

The half maximal inhibitory concentration (IC$_{50}$) is used to measure the effectiveness of a compound in inhibiting the biological activity. In order to assess reversible inhibition potential, IC$_{50}$ values are taken from the inhibitor candidates and competition binding assays, which are well-known in the art, are performed. The IC$_{50}$ value should be essentially the same for any incubation time.

In a further embodiment of the diagnostic device of the invention, the binding agent A is an inhibitor of the enzyme activity of glutamate carboxypeptidase II. Preferably the inhibition of the enzyme activity of glutamate carboxypeptidase II is reversible.

In another embodiment, the invention relates to the diagnostic device as described herein, wherein A has the following structural formula II:

wherein X is a bond, NH or O,

R$_1$, R$_2$, R$_3$, R$_4$ and R$_5$ are independently selected from the group consisting of: hydrogen alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, 4° ammonium ion, primary ketamine, secondary ketamine, primary aldimine, secondary aldimine, imide, azide, azo (diimide), cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphine, phosphono, phosphate, borono, boronate, borino, and borinate.

R$_1$, R$_2$, R$_3$, R$_4$ and R$_5$ may be unsubstituted or substituted by one or more chemical groups, such as alkyl, alkenyl, alkynyl, or halo, as long as it has no negative impact on the inhibitory activity.

Preferably R$_1$ and/or R$_2$ in formula II is substituted by or bound to the linker molecule L The terms "alkyl", "alkenyl" and "alkynyl", as used herein, include within their scope straight chain, branched chain and cyclic moieties. The terms "alkenyl" and "alkynyl" are intended to include one or more unsaturated bonds. Preferably, the "alkyl", "alkenyl" and "alkynyl" are "C$_{1-6}$-alkyl", "C$_{2-6}$-alkenyl" and "C$_{2-6}$-alkynyl" groups.

In another embodiment, the invention relates to the diagnostic device as described herein, wherein R$_1$ or R$_2$ as defined herein is a group bonded covalently or non-covalently to L.

A preferred embodiment of the invention relates to the herein described diagnostic device, wherein A has the following structural formula III:

The herein described binding agent A may be bound to the substrate directly or indirectly through linker technologies using various strategies. Preferably the nitrogen bound hydrogen in formula III is substituted by or bound to the linker molecule L.

The binding agent A may be bound to the substrate through adhesion, electrostatic interaction, chemically linkage, or covalent or non-covalent binding. These strategies include standard streptavidin-biotin interaction. It also includes the direct binding of (monoclonal) antibodies like IgG or fragments thereof to the substrate via adhesion or electrostatic interaction. In addition, covalent linkage of target-specific molecular structures like enzymes, antibodies or fragments thereof, nucleic acids, peptides or glycopeptides could be performed using linker technology as described in detail below. The latter technique allows the precise binding of target structures to substrate giving nanometer scale spatial resolution and therefore provides accurate real-time information regarding the concentration and spatial distribution.

Preferably A is bound to the substrate indirectly through linker technologies, e.g. via polymeric or protein structures, such as alginat, hydrogel (e.g., Xantec Hydrogel), or biotin/streptavidin.

In a further embodiment, the linker compound L of the diagnostic device of the invention is a polymer, protein, preferably alginate or hydrogel.

According to a further embodiment of the invention, the binding agent A is conjugated to a detectable marker, preferably a fluorescent dye or a chemiluminescent dye or a radiotracer, or the binding agent A is conjugated to a drug. Preferably, the drug is an anti cancer drug.

The term "detectable marker" as used herein includes, but is not limited to, a chromophore, an enzyme, an enzyme reactive compound whose cleavage product is detectable, rhodamine, biotin, streptavidin, a fluorescent compound, a chemiluminscent compound, and derivatives and/or combinations of these markers. In the examples provided, biotin-avidin was used. Labeling with any marker is carried out under conditions for obtaining optimal detection and binding of the binding agent.

The binding agent can be coupled to a signal transmitter.

Examples for signal transmitters can be from the group of Fluorophores. Fluorophore molecules could be either utilized alone, or serve as a fluorescent motif of a functional system. Based on molecular complexity and synthetic methods, fluorophore molecules could be generally classified into four categories: proteins and peptides, small organic compounds, synthetic oligomers and polymers, and multi-component systems. Fluorescent proteins can be green fluorescent protein (GFP), YFP (yellow fluorescent protein) and RFP (red fluorescent protein). Non-protein organic fluorophores belong to following major chemical families: Xanthene derivatives like fluorescein, rhodamine, Oregon green, eosin, and Texas red; cyanine derivatives like cyanine, indocarbocyanine, oxacarbocyanine, thiacarbocyanine, and merocyanine; Naphthalene derivatives (dansyl and prodan derivatives); Coumarin derivatives; oxadiazole derivatives like pyridyloxazole, nitrobenzoxadiazole and benzoxadiazole; Pyrene derivatives like cascade blue etc.; Oxazine derivatives like Nile red, Nile blue, cresyl violet, oxazine 170 etc.; Acridine derivatives like proflavin, acridine orange, acridine yellow etc.; Arylmethine derivatives like auramine, crystal violet, malachite green; Tetrapyrrole derivatives like porphin, phthalocyanine and bilirubin. Further signal transmitters can be from the group of semiconductors like quantum dots.

Other signal transmitters can be radiotracers or high payload Magnetic resonance imaging (MRI) contrast agents that can be for noninvasive molecular imaging techniques such as MRI, Single photon emission computed tomography (SPECT) and Positron emission tomography (PET). Typical isotopes include $^{11}$C, $^{13}$N, $^{15}$O, $^{18}$F, $^{64}$Cu, $^{62}$Cu, $^{124}$I, $^{76}$Br, $^{82}$Rb, $^{68}$Ga, $^{99m}$Tc, $^{111}$In, $^{123}$I and $^{201}$TI.

Furthermore, enzymes like horse radish peroxidase (HRP) coupled to the binding agent can be used as signal transmitters.

In another embodiment, the diagnostic device of the invention comprises a substrate (herein indicated as B), wherein the substrate comprises a metallic carrier. Preferably, the metallic carrier is composed of stainless steel. The substrate of the device of the invention may be a planar or non planar substrate made of a metal, such as stainless steel, a polymer, such as silicon or biocompatible polymers or glass, and could be in general transparent, non-transparent, conductive, semiconductive or non-conductive. The substrates could be biocompatible for in vivo applications of the sensor.

In a further embodiment, the diagnostic device of the invention comprises an interlayer assembled on the substrate B. Preferably, the interlayer is composed of a noble metal like gold, platinum or silver. Preferably, the substrate comprises an interlayer composed of metal, preferably a metal of the $10^{th}$ or $11^{th}$ group of the periodic table of elements, preferable those mentioned in the International publication WO 2006/131400 A1. However, the substrate may also comprise further layers such as polymeric layers.

Accordingly, the diagnostic device may further comprise a secondary layer assembled on the substrate B with the following properties: The secondary layer is formed as a polymeric layer, preferably composed of hydogel. The secondary layer facilitates binding of the binding agent, e.g. the inhibitors defined in formula II or III. The polymeric layer facilitates enrichment of target molecules or cells due to the increase of surface area. The secondary layer may further contain functional groups for covalent binding of the binding agent, such as the detectable compounds defined herein above. The secondary layer may further contain enzyme reactive compounds whose cleavage product is detectable for facilitating quantitative detection and production of target molecules or cells. The secondary layer may serve as a matrix that prevents binding of unspecific cells and undesired interaction with bodily fluids. The binding agent, e.g. the inhibitors defined in formula II or III may covalently bind to said inter layer.

In order to improve the efficiency of the diagnostic device, the functionalized surface area (functionalized for effective binding to the binding agent) or the surface area of the substrate itself may be increased by using specific surface structures. The surface structures may include ridges, cavities, protrusions, edges or grooves, which may be of cylindrical, spherical, conical, or pyramid shape.

Further exemplary substrates and methods for producing the same can be found in the International publications Nos.: WO 2010/145824 A1, WO 2011/113584 A1, and in the European patent EP 1811302 B1. An exemplary approach of preparing the device of the present invention is given in the Example section, below.

In a further embodiment, the invention relates to a method for detecting bio markers in a fluid or tissue comprising the steps: a) contacting the binding agent of formula II or III or the diagnostic device of the invention comprising said binding agent with bodily fluid sample; b) allowing the A to bind to the biomarker in the bodily fluid; and c) detecting the presence of A, thereby detecting biomarkers that bind directly or indirectly to the bound biomarker bound to A. For instance PSMA binds to an inhibitor serving as a binding agent (A). In view of the fact that PSMA is part of a cell, also other parts of the cell may be detected, which are not PSMA. An exemplary approach for an in vivo application as well as an in vitro application for preparing the substrate of the present invention is given in the Example section, below In a further embodiment, the invention relates to a kit for detecting or capture disease related bio markers in a fluid or tissue comprising: a) the diagnostic device of the invention, and b) instructions for its use.

In a further embodiment, the invention relates to the use of the binding agent of formula II or III or the diagnostic device of the invention comprising said binding agent for the detection of specific disease related target structures. In another embodiment, the invention relates to the use of the binding agent of formula II or III for the isolation of specific disease related target structures.

EXAMPLES

Example 1

Production of the Diagnostic Device

The production of the diagnostic device is performed by four separate but interrelated procedures. The first step is the production of the binding agent, the second step is the production of the substrate, and the third step is functionalizing the substrate using the binding agent of the invention, which is bound to the substrate directly or indirectly through linker technologies, and optionally removing the bio molecule bound to the binding agent. For example, the substrate is produced by deposition of nanostructures like nanopatterned metal, semiconductors and/or magnetic-islands on planar or non-planar, transparent or non-transparent surface, wherein the nanostructures are distributed on the surface, and subsequent the binding agent is bound to the nanostructures to provide the device as schematically shown in FIG. 2.

A. Production of the Binding Agent

Figure 2:
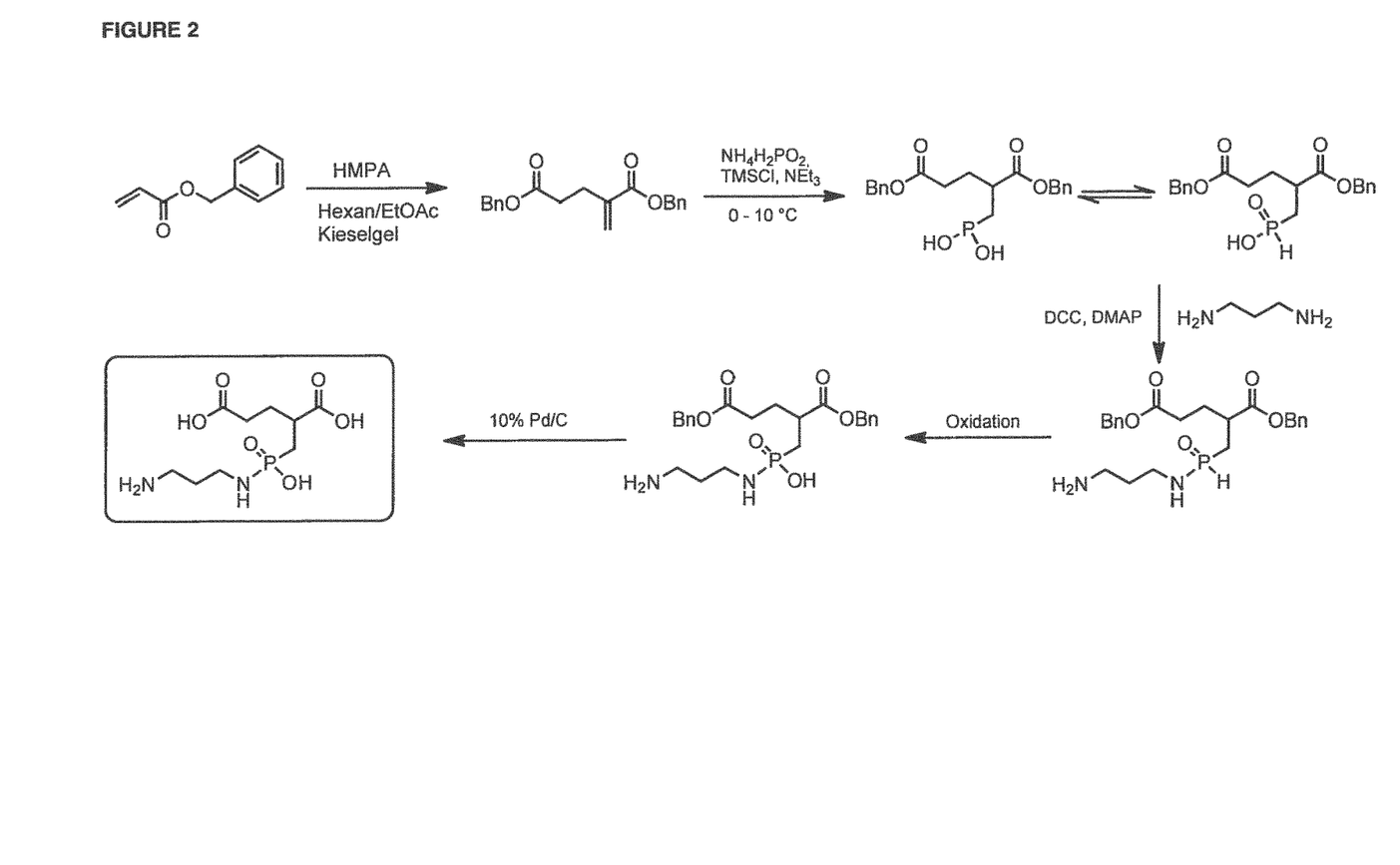
FIG. 2 shows an overview of the synthesis protocol of an exemplary inhibitor.

FIG. 2 is an overview of the synthesis protocol.

Product 1 ($C_{20}H_{20}O_4$; 324.36 g/mol)

20 g of benzylacrylate (0.12 mol) were placed under argon atmosphere into a heated-off flask, which was then heated to 100° C. The heat source was removed and 0.4 g (0.45 ml; 2.14 mmol) tris(dimethylamino)phosphin were dropwise added to the solution, whereby the reaction mixture was heated to 115° C. The resulting yellow solution was cooled down to room temperature. Followed by adding 75 ml of silica gel pulp (hexan:ethyl acetate 5:1). The mixture was placed on dry silica gel and washed with hexan/ethal acetate 1:1. The solution was removed by the use of an evaporator, and the reduced coulourless liquid was dried overnight by lyophilisation. The product yield of product 1 was 15.97 g (0.049 mol), which corresponds to a yield of 82%.

(Synthesis was analogue to: P. F. Jackson et al, Design and pharmacological activity of phosphinic acid based NAALADase inhibitors, J. Med. Chem. 2001, 44, 4170-4175)

Product 2 ($C_{20}H_{23}O_6P$; 390.29 g/mol)

In a heated flask a suspension of ammonium hypophosphite (12.86 g, 0.155 mol) was prepared in dichloromethane (245 ml). To this suspension, trimethylsilyldiloride (44.54 g; 0.41 mol; 51.8 ml) and triethylamine (37.64 g; 0.37 mol; 51.6 ml) were added, whereby the temperature stayed under 10° C. This mixture was stirred at 3-9° C. for 30 minutes. After that, Product 2 (10 g; 0.031 mol, dissolved in 10.2 ml DCM) was added at a temperature of under 10° C. The solution was warmed up to room temperature and stirred for 20.5 h. Next, the reaction was stopped by careful additions of 3 N HCl (112 ml) whereby the temperature was kept under 25° C. The organic phase was washed four times with 3 N HCl (per 55 ml) and four times with $H_2O$ (per 55 ml). The solvents were removed from the rotary evaporator and the mixture was dried overnight in the freeze drying system. The result was 9,866 g (0.0253 mol) of a cloudy, colourless and viscous liquid which corresponds to a yield of 81%.

(Synthesis following: D. Vitharana et al, Synthesis and biological evaluation of (R)- and (S)-2-(phosphonomethyl)pentanedioic acids as inhibitors of glutamate carboxypeptidase II, Tetrahedron Assymetry 2002, 13, 1609-1614.)

Product 3 ($C_{23}H_{31}O_5N_2P$; 446.41 g/mol)

Product 2 (4.64 g, 11.9 mmol) was dissolved in DMF (23.8 ml (2 ml/mmol)) and stirred in an ice bath under argon atmosphere with Diaminopropan (1.99 ml, 23.8 mmol) for 30 minutes. After that, DMAP (0.279 g, 2.38 mmol) and DCC (2.27 g, 11.9 mmol) were added to the solution and stirred under argon atmosphere at RT for 2.5 h. The solvent was removed from the rotary evaporator. Next, a column chromatographic treatment with DCM/MeOH at a ration of 9/1 was made. In a final Stepp, product 3 was lyophilisied. Here the result was 4,562 g (0.010 mol) of a yellow, solid oil which corresponds to a yield of 84%.

Product 4 ($C_{23}H_{31}O_6N_2P$; 462.47 g/mol)

Product 3 (4,562 g, 9.62 mmol) was dissolved in a water/acetonitrile solvent (1:1, 60 ml). After that a 0.1 mole oxidation solution (0.1 M iodine in THF/water/pyridine 7:2:1) was added slowly in drops until the red-brown colour remained. Next, the solution was evaporated to dryness and absorbed in DCM. The organic phase was shaken out several times with 5% solution of $NaHSO_4$ and saturated NaCl solution. The watery phase was extracted with DCM. The collected organic phases were dried with $NaSO_4$ and were filtered out. The generated solution was removed from the rotary evaporator and dried in the freeze drying system. The result was 2.6 g (5.63 mmol) of a brownish foam which corresponds to a yield of 58.5%.

(Synthesis following: D. Vitharana et al, Synthesis and biological evaluation of (R)- and (S)-2-(phosphonomethyl) pentanedioic acids as inhibitors of glutamate carboxypeptidase II, Tetrahedron Assymetry 2002, 13, 1609-1614.)

Product 5 ($C_9H_{19}O_6N_2P$; 282.23 g/mol)

Product 4 (1 g, 2.04 mmol) was stirred under hydrogen gas (6 balloons) with a 500 mg Pd/C catalyst in a water/acetonitrile solution (18 ml/ 7 ml) for 20 h. After that the catalyst was filtered out and the filtrate was coevaporated. The cleaning of the educt took place by use of HPLC. (Buffer A: 5% MeCN, buffer B: 30% MeCN)

(Synthesis following: D. Vitharana et al, Synthesis and biological evaluation of (R)- and (S)-2-(phosphonomethyl) pentanedioic acids as inhibitors of glutamate carboxypeptidase II, Tetrahedron Asymmetry 2002, 13, 1609-1614.)

B. Production of the Substrate

As a substrate, a detection catheter was used. The detection catheter has been prepared in accordance with the protocols disclosed in WO 2010/145824, which is incorporated by reference herein.

C. Functionalizing the Substrate

To functionalize the above nanoparticle substrate, the binding molecule, e.g. the inhibitor of formula III is bound to surfaces using various strategies. These strategies include standard streptavidin-biotin interaction. It also may include the direct binding of (monoclonal) antibodies like IgG or fragments there of to the array surface via adhesion or electrostatic interaction. In addition, covalent linkage of target-specific molecular structures like antibodies or fragments there of, oligomers made of nucleic acids, or peptide or glycopeptides could be performed using linker technology as described in the detailed example below. The diagnostic device of the invention is suitable for medical application, for biological and biochemical research, as well as for environmental monitoring and protection and food safety. Concerning medical application, the diagnostic device is assembled as a device for in vivo and in vitro use.

D. Recovering of the Binding Agent for Further use

After the biomarkers have been isolated by means of the binding agent A of the invention, the biomarker may be removed from the binding agent A by the addition of the binding agent of the invention in high concentration, or an enzymatic cleavage of the linker molecule, thus allowing a determination of the biomarker in vitro.

Example 2

In vivo detection

For the in vivo detection using the diagnostic device, the device is assembled on a spring wire carrier providing a molecular or cell select catheter to obtain rare molecular or cellular components directly out of the circulation or the body in general. As a device for in vivo appliance, the device assembled on e.g. spring wires provides a cell or molecular select catheter which is useful for various applications, e.g. cancer diagnosis and the monitoring of chronic diseases like cancer, metabolic, infectious, allergic and inflammatory diseases. This device is applied by puncture of a blood vessel (vein or artery), e.g., by using a hollow needle; and putting the device through the hollow needle or through a standard venous line into the blood vessel. After an appropriate incubation time (between 5 to 60 minutes) the device is replaced with the attached cells and/or molecules for further processing.

As a cell select catheter, the diagnostic device according to the invention is suitable for the isolation of rare cells out of the peripheral blood, e.g. circulating tumor cells (CTCs) or bacteria.

CTCs are cells that appear only in the blood of humans or animals that have cancer. The cell select catheter equipped with a binding agent that is directed against cellular and soluble PSMA binds specifically-PSMA protein on PSMA positive cells or soluble PSMA in blood. The number of bound cells to the cell select catheter depends on the retention period in the blood circulation and the actual cell concentration. Appropriate numbers of PSMA positive cells for monitoring a patient before or during therapy and/or after finishing a course of cancer medication and/or diagnoses of chromosomal aberration and/or other genetic defects, could be collected after a retention period of 5-60 minutes in vivo. After replacing the catheter, the tip of the catheter with the attached cells is placed into a collector tube for transport to specialized laboratories.

Example 3

In vitro Detection

The binding agent can be bound to various linkers and surfaces and in this context be used in various in vitro applications.

The "diagnostic device" for in vitro use is assembled on planar and transparent support to give a "lab on a chip" allowing quantitative and qualitative determination of targets by measuring the plasmon resonance frequencies on the nanostructured surfaces or luminescence or magnetic properties depending on the material that is deposited onto the support using nanosphere lithography. As a device for in vitro appliance, the "diagnostic device" is for "on scene" diagnostic procedures (e.g. at the bedside, in the operating theatre, the ambulance, or the battle field) that should be used as described below. According to the quantum size confinement effect, nanosized metallic particles show different optical absorption spectra depending on size. The surface plasmon band is due to collective electron oscillation around the surface of the particles. For example Ag (Silver) nanoparticles have plasmon band around 390 nm while Au nanoparticles have the plasmon band around 520 nm. The pick position, intensity and bandwidth of the surface plasmon absorption are directly related to size, morphology (shape), and surface functionality of the particles. By covering the 2-dimensional assemblies of gold nanoparticles with avidin their plasmon peak shifts toward longer wavelength and can be easily detected. The invention may be further illustrated by the following examples.

The binding agent can be coupled to signal transmitters and used to detect the biomarker. For example it can be coupled to fluorescein isothiocyanate (FITC). The bound binding agent can be detected in this example by exciting the FITC using light with a wavelength around 480 nm and detected using an appropriate filter that can detect wavelengths around 525 nm.

Figure 3:
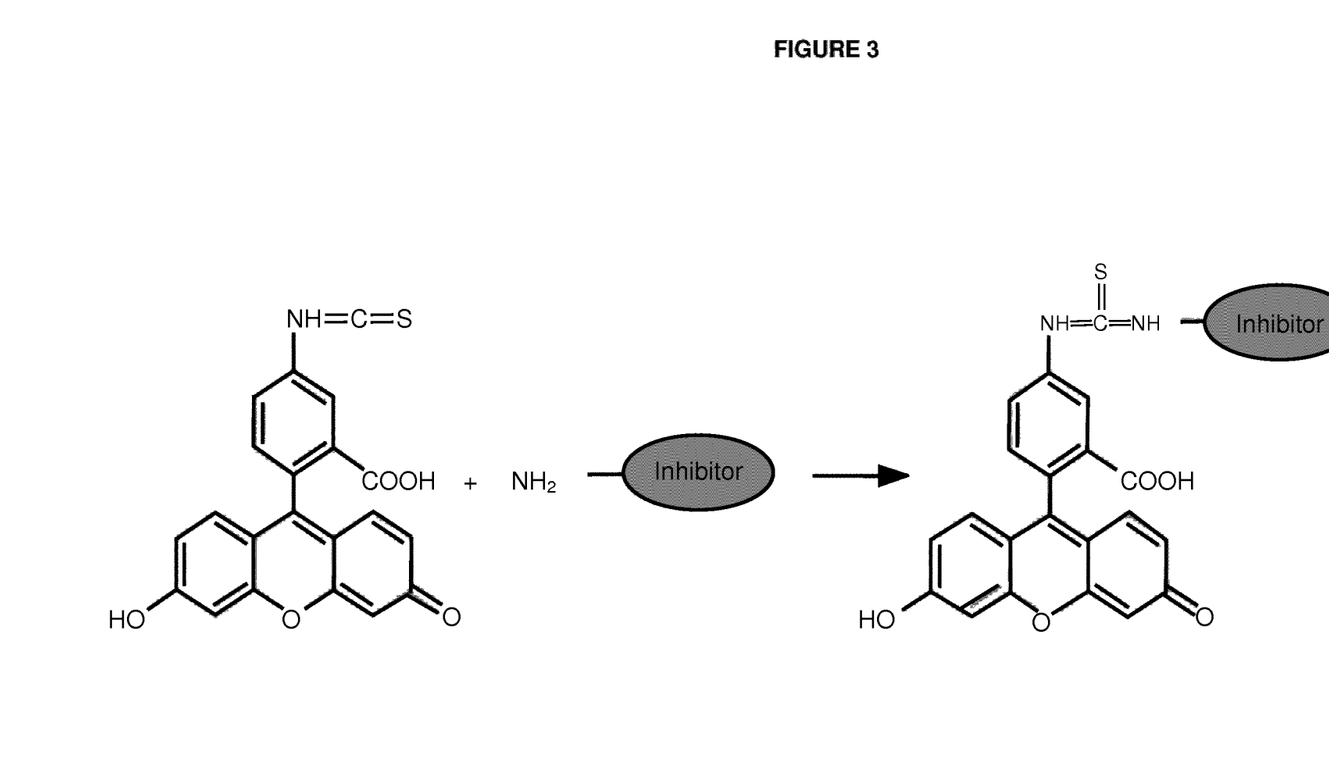
FIG. 3 shows an example of the binding agent coupled to fluoresceinisothiocyanat (FITC)
Figure 4:
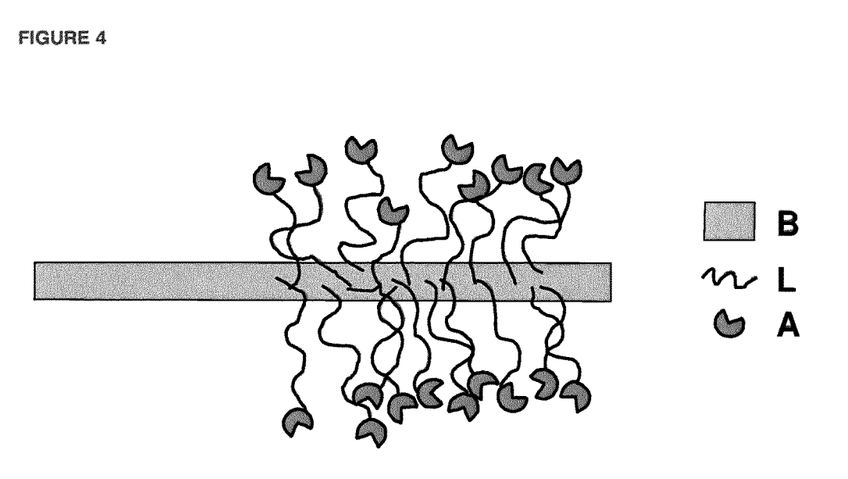
FIG. 4 shows a schematic illustration of the diagnostic device of the invention.

FIG. 3 is an example of the binding agent coupled to Fluoresceinisothiocyanate (FITC).

The binding agent can be coupled to surfaces to isolate a biomarker from a fluid sample, such as urine or blood.

The invention claimed is:

1. A diagnostic device for in vivo and/or in vitro detection of a bio marker in a fluid or tissue, wherein the diagonostic device comprises a composition having the formula I:

A-L-B, wherein A is a binding agent that specifically binds said bio marker, and wherein A is an enzyme inhibitor, and wherein A has the following structural formula III:

(III)

L is a linker; and
B is a substrate comprising a metallic, a semiconductor, or a polymeric carrier.

2. The diagnostic device of claim 1, wherein L comprises a polymer or protein.

3. The diagnostic device of claim 1, wherein A is conjugated to a detectable marker or a drug.

4. The diagnostic device of claim 3, wherein the detectable marker or drug comprises a fluorescent dye, a chemiluminescent dye, a radiotracer or an anti cancer drug.

5. A method for detecting bio markers in a fluid or tissue comprising the steps:
contacting the diagnostic device of claim 1 with a bodily fluid sample or tissue;
allowing A to bind to the bio marker in the bodily fluid or tissue; and
detecting the presence of A.

6. A kit for detecting disease related bio markers in a fluid or tissue comprising:
the diagnostic device of claim 1, and
instructions for its use.

7. A method for detecting specific disease related target structure, comprising contacting the diagnostic device of claim 1 with a bodily fluid sample or tissue; and detecting the presence of A, wherein the binding agent A has a target structure related to a disease.

8. The diagnostic device of claim 1, wherein L comprises alginate.

9. The diagnostic device of claim 1, wherein L comprises hydrogel.

10. A method for detecting bio markers in a fluid or tissue comprising the steps:
contacting a binding agent A of formula III

III with a bodily fluid sample or tissue,
allowing A to bind to the bio marker in the bodily fluid or tissue; and
detecting the presence of A.

11. A method for detecting specific disease related target structure in a fluid or tissue comprising:
contacting a binding agent of formula III with a bodily fluid sample or tissue; and
detecting the presence of the binding agent, which has a target structure related to a disease.

12. The diagnostic device of claim 1, wherein the bio marker has a target structure which is present on a circulating tumor cell (CTC) in a bodily fluid.

13. The diagnostic device of claim 1, wherein the target structure is glutamate carboxypeptidase II.

14. The diagnostic device of claim 1, wherein A has a target structure related to a disease.

15. The diagnostic device of claim 14, wherein the disease is cancer or infection.

16. The diagnostic device of claim 13, wherein inhibition of the enzyme activity of glutamate carboxypeptidase II is reversible.

* * * * *

UNITED STATES PATENT AND TRADEMARK OFFICE
CERTIFICATE OF CORRECTION

PATENT NO.        : 10,352,931 B2
APPLICATION NO.   : 14/914875
DATED             : July 16, 2019
INVENTOR(S)       : Björn Nowack Page 1 of 1

It is certified that error appears in the above-identified patent and that said Letters Patent is hereby corrected as shown below:

In the Claims

Column 25, Line 35, Claim 1, delete "diagonostic" and insert -- diagnostic --

Column 26, Line 55, Claim 10, after "III" insert -- ; --

Column 27, Line 6, Claim 11, after "III" insert -- ; --

Signed and Sealed this
Seventeenth Day of September, 2019

Andrei Iancu
*Director of the United States Patent and Trademark Office*